(12) United States Patent
Cladingboel

(10) Patent No.: US 7,314,931 B2
(45) Date of Patent: Jan. 1, 2008

(54) CHEMICAL INTERMEDIATE

(75) Inventor: David Cladingboel, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 92 days.

(21) Appl. No.: 10/532,223

(22) PCT Filed: Oct. 13, 2003

(86) PCT No.: PCT/SE03/01594

§ 371 (c)(1),
(2), (4) Date: Mar. 17, 2006

(87) PCT Pub. No.: WO2004/035592

PCT Pub. Date: Apr. 29, 2004

(65) Prior Publication Data

US 2006/0199814 A1    Sep. 7, 2006

(30) Foreign Application Priority Data

Oct. 14, 2002    (GB) .................................. 0223712.1

(51) Int. Cl.
*C07D 498/08* (2006.01)
*A61K 31/5386* (2006.01)

(52) U.S. Cl. ..................... 544/74; 514/230.5
(58) Field of Classification Search .................. 544/74
See application file for complete search history.

(56) References Cited

FOREIGN PATENT DOCUMENTS

| WO | WO-01/28992 A2 | 4/2001 |
|---|---|---|
| WO | WO-02/083690 A1 | 10/2002 |

OTHER PUBLICATIONS

Chapman et al., "Difluoramination of Heterocyclic Ketones: Control of Microbasicity," J. Org. Chem. 63:1566-1570 (1998).

Chapman et al., "Nitrolysis of a Highly Deactivated Amide by Protonitronium. Synthesis and Structure of HNFX[1]," J. Org. Chem. 64:960-965 (1999).

Dave et al., "Facile Preparation of 3,7-Diazabicyclo[3.3.0]octaine and 3,7,10Triheterocyclic [3.3.3]Propellane Ring Systems from 1,5-Diazacyclooctane 3,7-Derivatives[1]," J. Org. Chem. 61:8897-8903 (1996).

Paudler et al., "3,7-Disubstituted Octahydro-1,5-diazocines. Their Conversion Into Tetrahydro-1,5-diazocines and into Ring-Contraced Products," J. Org. Chem 32:2425-2430 (1967).

Paudler et al., "1,5-Bis(p-toluenesulfonyl)-3,7-Dihydroxyoctahydro-1,5-diazocine," J. Org. Chem. 31:277-280 (1966).

Stetter et al., "Synthese des 1.3-Diaza-6-oxa-adamantans," Chem. Ber. 96(11):2827-2831 (1963).

PCT/SE2003/001594 International Search Report (Jan. 12, 2004).

*Primary Examiner*—Kahsay Habte
(74) *Attorney, Agent, or Firm*—Christer Hallgren; Pepper Hamilton LLP

(57) ABSTRACT

Compounds of Formula I, wherein $R^2$ represents $C_{1-6}$ alkyl (optionally substituted by one or more substituents selected from —OH, halo, cyano, nitro and aryl) or aryl, wherein each aryl and aryloxy group, unless otherwise specified, is optionally substituted, and methods of preparation thereof are disclosed

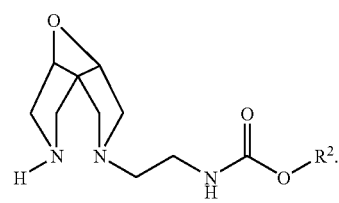

I

10 Claims, No Drawings

CHEMICAL INTERMEDIATE

RELATED APPLICATIONS

This application is a national stage filing under 35 U.S.C. 371 of International Application PCT/SE2003/001594, filed Oct. 13, 2003, which claims priority from United Kingdom Patent Application No. 0223712.1, filed Oct. 14, 2002, the specification of which is incorporated by reference herein. International Application PCT/SE2003/001594 was published under PCT Article 21(2) in English.

FIELD OF THE INVENTION

This invention relates to novel intermediates and their use in a process for the preparation of oxabispidine compounds.

BACKGROUND OF THE INVENTION

The number of documented compounds-including the 9-oxa-3,7-diazabicyclo-[3.3.1]nonane (oxabispidine) structure is very few. As a result, there are very few known processes that are specifically adapted for the preparation of oxabispidine compounds.

Certain oxabispidine compounds are disclosed in *Chem. Ber.* 96(11), 2827 (1963) as intermediates in the synthesis of 1,3-diaza-6-oxa-adamantanes.

Hemiacetals (and related compounds) having the oxabispidine ring structure are disclosed in *J. Org. Chem.* 31, 277 (1966), ibid. 61(25), 8897 (1996), ibid. 63(5), 1566 (1998) and ibid. 64(3), 960 (1999) as unexpected products from the oxidation of 1,5-diazacyclooctane-1,3-diols or the reduction of 1,5-diazacyclooctane-1,3-diones.

1,3-Dimethyl-3,7-ditosyl-9-oxa-3,7-diazabicyclo[3.3.1] nonane is disclosed in *J. Org. Chem.* 32, 2425 (1967) as a product from the attempted acetylation of trans-1,3-dimethyl-1,5-ditosyl-1,5-diazacyclooctane-1,3-diol.

International patent application WO 01/28992 describes the synthesis of a wide range of oxabispidine compounds, which compounds are indicated as being useful in the treatment of cardiac arrhythmiias. Amongst the compounds disclosed are a number that bear a N-2-(tert-butoxycarbonylamino)ethyl substituent.

International patent application WO 02/083690 discloses inter alia a process for the preparation of a compound of formula I,

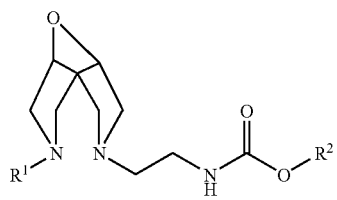

wherein $R^1$ represents H or an amino protective group and $R^2$ represents $C_{1-6}$ alkyl (optionally substituted and/or terminated by one or more substituents selected from —OH, halo, cyano, nitro and aryl) or aryl, wherein each aryl and aryloxy group, unless otherwise specified, is optionally substituted;

which process comprises reaction of a compound of formula II,

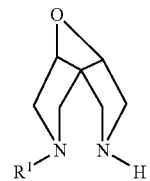

wherein $R^1$ is as defined above, with either:
(i) a compound of formula III,

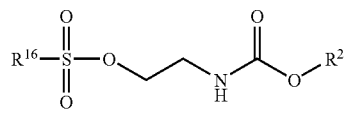

wherein $R^{16}$ represents unsubstituted $C_{1-4}$ alkyl, $C_{1-4}$ perfluoroalkyl or phenyl, which latter group is optionally substituted by one or more substituents selected from $C_{1-6}$ alkyl, halo, nitro and $C_{1-6}$ alkoxy, and $R^2$ is as defined above; or
(ii) acrylamide, followed by reaction of the resulting intermediate of formula IV,

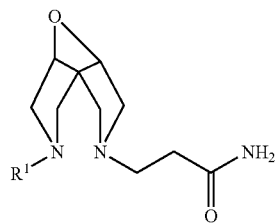

wherein $R^1$ is as defined above, with an alcohol of formula $R^2$—OH and an agent that promotes, or agents that in combination promote, rearrangement and oxidation of the compound of formula IV to an intermediate isocyanate, which may then react with the alcohol of formula $R^2$—OH, wherein $R^2$ is as defined above.

The above application also discloses a process for the preparation of a compound of formula I in which $R^1$ represents H, which comprises the preparation of a corresponding compound of formula I in which $R^1$ represents an amino protective group by processes described therein, followed by removal of the amino protective group from that compound. It also discloses in Example 3 Alternative II that [2-(7-benzyl-9-oxa-3,7-diazabicyclo[3.3.1]-non-3-yl)ethyl] carbamic acid tert-butyl ester 2,4,6-trimethylbenzenesulfonic acid salt was converted into the free base with aqueous sodium hydroxide. The [2-(7-benzyl-9-oxa-3,7-diazabicyclo[3.3.1]non-3-yl)-ethyl]carbamic acid tert-butyl ester obtained was hydrogenated in the presence of citric acid and 5% Pd/C to give [2-(9-oxa-3,7-diazabicyclo[3.3.1] non-3-yl)ethyl]carbamic acid tert-butyl ester which was reacted directly without further purification to give (2-(7-[3-(4-cyanoanilino)propyl]-9-oxa-3,7-diazabicyclo[3.3.1] non-3-yl)-ethyl)carbamic acid tert-butyl ester.

DESCRIPTION OF THE INVENTION

Certain novel solid salts of have now been found which offer advantages over known methods.

According to a first aspect of the invention there is provided acid addition salts of compounds of Formula I

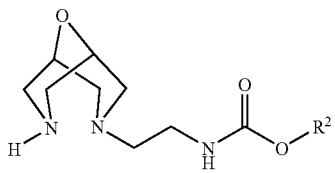

wherein $R^2$ represents $C_{1-6}$ alkyl (optionally substituted and/or terminated by one or more substituents selected from —OH, halo, cyano, nitro and aryl) or aryl, wherein each aryl and aryloxy group, unless otherwise specified, is optionally substituted.

In a first aspect the acid component of the acid addition salt is represented by formula A

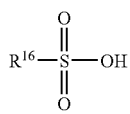

wherein $R^{16}$ represents unsubstituted $C_{1-4}$ alkyl, $C_{1-4}$ perfluoroalkyl or phenyl, which latter group is optionally substituted by one or more substituents selected from $C_{1-6}$ alkyl, halo, nitro and $C_{1-6}$ alkoxy, and $R^2$ is as defined above. Specific salts that may be mentioned include toluenesulfonate, benzenesulfonate, nosylate, brosylate, besylate and mesitylate.

In one aspect the salts are in solid form.

In another aspect the salt is [2-(9-oxa-3,7-diazabicyclo[3.3.1]non-3-yl)-ethyl]-carbamic acid tert-butyl ester 2,4,6-trimethylbenzenesulfonic acid.

In a further aspect the present invention provides a process for the preparation of a compound of Formula II

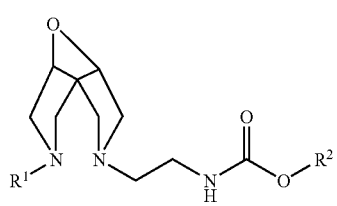

wherein $R^1$ represents a structural fragment of formula Ia

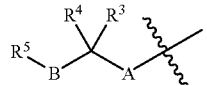

in which A represents $CH_2$ and $R^3$ represents —OH or —N(H)$R^7$;

$R^4$ represents H, $C_{1-6}$ alkyl or, together with $R^3$, represents =O;

$R^5$ represents phenyl or pyridyl, both of which groups are optionally substituted by one or more substituents selected from —OH, cyano, halo, nitro, $C_{1-6}$ alkyl (optionally terminated by —N(H)C(O)O$R^{13a}$), $C_{1-6}$ alkoxy, —N($R^{14a}$)$R^{14b}$, —C(O)$R^{14c}$, —C(O)O$R^{14d}$, —C(O)N($R^{14e}$)$R^{14f}$, —N($R^{14g}$)C(O)$R^{14h}$, —N($R^{14i}$)C(O)N($R^{14j}$)$R^{14k}$, —N($R^{14m}$)S(O)$_2$$R^{13b}$, —S(O)$_2$$R^{13c}$ and/or —OS(O)$_2$$R^{13d}$;

$R^7$ represents H, $C_{1-6}$ alkyl, —E-aryl, —E-Het$^1$, —C(O)$R^{9a}$, —C(O)O$R^{9b}$, —S(O)$_2$$R^{9c}$, —[C(O)]$_p$N($R^{10a}$)$R^{10b}$ or —C(NH)NH$_2$;

$R^{9a}$ to $R^{9d}$ independently represent, at each occurrence when used herein, $C_{1-6}$ alkyl (optionally substituted and/or terminated by one or more substituents selected from halo, aryl and Het$^2$), aryl, Het$^3$, or $R^{9a}$ and $R^{9d}$ independently represent H;

$R^{10a}$ and $R^{10b}$ independently represent, at each occurrence when used herein, H or $C_{1-6}$ alkyl (optionally substituted and/or terminated by one or more substituents selected from halo, aryl and Het$^4$), aryl, Het$^5$, or together represent $C_{3-6}$ alkylene, optionally interrupted by an O atom;

E represents, at each occurrence when used herein, a direct bond or $C_{1-4}$ alkylene;

B represents —Z—, —Z-N($R^{12}$)—, —N($R^{12}$)-Z—, —Z—S(O)$_n$— or —Z-O—(in which latter two groups, Z is attached to the carbon atom bearing $R^3$ and $R^4$);

Z represents a direct bond or $C_{1-4}$ alkylene;

$R^{11}$ and $R^{12}$ independently represent H or $C_{1-6}$ alkyl;

$R^{13a}$ to $R^{13d}$ independently represent $C_{1-6}$ alkyl;

$R^{14a}$ and $R^{14b}$ independently represent H, $C_{1-6}$ alkyl or together represent $C_{3-6}$ alkylene, resulting in a four- to seven-membered nitrogen-containing ring;

$R^{14c}$ to $R^{14m}$ independently represent H or $C_{1-6}$ alkyl; and n represents 0, 1 or 2;

p represents 1 or 2;

Het$^1$ to Het$^5$ independently represent, at each occurrence when used herein, five- to twelve-membered heterocyclic groups containing one or more heteroatoms selected from oxygen, nitrogen and/or sulfur, which heterocyclic groups are optionally substituted by one or more substituents selected from =O, —OH, cyano, halo, nitro, $C_{1-6}$ alkyl, $C_{1-6}$ alkoxy, aryl, aryloxy, —N($R^{15a}$)$R^{15b}$, —C(O)$R^{15c}$, —C(O)O$R^{15d}$, —C(O)N($R^{15e}$)$R^{15f}$, —N($R^{15g}$)C(O)$R^{15h}$ and —N($R^{15i}$)S(O)$_2$$R^{15j}$;

$R^{15a}$ to $R^{15j}$ independently represent $C_{1-6}$ alkyl, aryl or $R^{15a}$ to $R^{15i}$ independently represent H;

and $R^2$ represents $C_{1-6}$ alkyl (optionally substituted and/or terminated by one or more substituents selected from —OH, halo, cyano, nitro and aryl) or aryl, wherein each aryl and aryloxy group, unless otherwise specified, is optionally substituted.

wherein a salt of a compound of Formula I

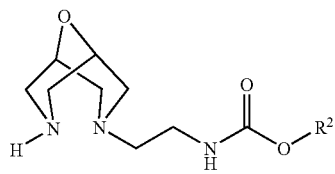

in which $R^2$ is a s previously defined is reacted with a compound of Formula III

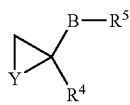

wherein Y represents O or $N(R^7)$ and $R^4$, $R^5$, $R^7$ and B are as hereinbefore defined, at a temperature in the range of 0° C. to 100° C. for example at elevated temperature (e.g. 60° C. to reflux) in the presence of a water and in the presence of a base, for example sodium carbonate.

In a first aspect the salt has been isolated in solid form prior to this process step.

A second aspect comprises a process for the preparation of tert-butyl 2-{7-[(2S)-3-(4-cyanophenoxy)-2-hydroxypropyl]-9-oxa-3,7-diaza-bicyclo[3.3.1]-non-3-yl}ethylcarbamate which comprises reacting a salt of [2-(9-oxa-3,7-diazabicyclo[3.3.1]non-3-yl)-ethyl]-carbamic acid tert-butyl ester with 4-[(2S)-oxiranylmethoxy]benzonitrile at a temperature in the range of 0° C. to 100° C. in the presence of water and in the presence of a base, for example sodium carbonate.

In another aspect of the process an isolated salt of [2-(9-oxa-3,7-diazabicyclo[3.3.1]non-3-yl)-ethyl]-carbamic acid tert-butyl ester is used particularly the 2,4,6-trimethylbenzenesulfonic acid salt.

The use of water as the reaction medium in the process has important advantages in terms of waste disposal and consequences for the environment.

The term "aryl", when used herein, includes $C_{6-10}$ aryl groups such as phenyl, naphthyl and the like. The term "aryloxy", when used herein includes $C_{6-10}$ aryloxy groups such as phenoxy, naphthoxy and the like. For the avoidance of doubt, aryloxy groups referred to herein are attached to the rest of the molecule via the O-atom of the oxy-group. Unless otherwise specified, aryl and aryloxy groups may be substituted by one or more substituents including —OH, cyano, halo, nitro, $C_{1-6}$ alkyl, $C_{1-6}$ alkoxy, —$N(R^{14a})R^{14b}$, —$C(O)R^{14c}$, —$C(O)OR^{14d}$, —$C(O)N(R^{14e})R^{14f}$, —$N(R^{14g})$ $C(O)R^{14h}$, —$N(R^{14m})S(O)_2R^{13b}$, —$S(O)_2R^{13c}$ and/or —$OS$ $(O)_2R^{13d}$ (wherein $R^{13b}$ to $R^{13d}$ and $R^{14a}$ to $R^{14m}$ are as hereinbefore defined). When substituted, aryl and aryloxy groups are preferably substituted by between one and three substitutents.

The term "halo", when used herein, includes fluoro, chloro, bromo and iodo.

Het ($Het^1$ to $Het^5$) groups that may be mentioned include those containing 1 to 4 heteroatoms (selected from the group oxygen, nitrogen and/or sulfur) and in which the total number of atoms in the ring system are between five and twelve. Het ($Het^1$ to $Het^5$) groups may be fully saturated, wholly aromatic, partly aromatic and/or bicyclic in character. Heterocyclic groups that may be mentioned include benzodioxanyl, benzodioxepanyl, benzodioxolyl, benzofuranyl, benzimidazolyl, benzomorpholinyl, benzoxazinonyl, benzothiophenyl, chromanyl, cinnolinyl, dioxanyl, furanyl, imidazolyl, imidazo[1,2-α]pyridinyl, indolyl, isoquinolinyl, isoxazolyl, morpholinyl, oxazolyl, phthalazinyl, piperazinyl, piperidinyl, purinyl, pyranyl, pyrazinyl, pyrazolyl, pyridinyl, pyrimindinyl, pyrrolidinonyl, pyrrolidinyl, pyrrolinyl, pyrrolyl, quinazolinyl, quinolinyl, tetrahydropyranyl, tetrahydrofuranyl, thiazolyl, thienyl, thiochromanyl, triazolyl and the like. Substituents on Het ($Het^1$ to $Het^5$) groups may, where appropriate, be located on any atom in the ring system including a heteroatom. The point of attachment of Het ($Het^1$ to $Het^5$) groups may be via any atom in the ring system including (where appropriate) a heteroatom, or an atom on any fused carbocyclic ring that may be present as part of the ring system. Het ($Het^1$ to $Het^5$) groups may also be in the N- or S-oxidised form.

The use of protecting groups is fully described in "Protective Groups in Organic Chemistry", edited by J. W. F. McOrnie, Plenum Press (1973), and "Protective Groups in Organic Synthesis", $3^{rd}$ edition, T. W. Greene & P. G. M. Wutz, Wiley-Interscience (1999). The process of the invention possesses the surprising advantage that compounds of formula I may be prepared conveniently from solid (as opposed to, for example, oily or semi-solid) precursors, which precursors may be purified using simple procedures (e.g. recrystallisation).

Further, the process of the invention may have the advantage that compounds of formula I may be prepared in higher yields, by way of fewer steps, in less time, more conveniently, and at a lower cost, than when prepared according to the process described in international patent application WO 01/28992.

The invention is illustrated, but in no way limited, by the following examples.

EXAMPLES

General Experimental Procedures

Mass spectra were recorded on one of the following instruments: a Waters ZMD single quad with electrospray (S/N mc350); a Perkin-Elmer SciX API 150ex spectrometer; a VG Quattro II triple quadrupole; a VG Platform II single quadrupole; or a Micromass Platform LCZ single quadrupole mass spectrometer (the latter three instruments were equipped with a pneumatically assisted electrospray interface (LC-MS)). $^1$H NMR and 13C NMR measurements were performed on Varian 300, 400 and 500 spectrometers, operating at $^1$H frequencies of 300, 400 and 500 MHz respectively, and at $^{13}$C frequencies of 75.5, 100.6 and 125.7 MHz respectively.

Rotamers may or may not be denoted in spectra depending upon ease of interpretation of spectra. Unless otherwise stated, chemical shifts are given in ppm with the solvent as internal standard.

Abbreviations
API=atmospheric pressure ionisation (in relation to MS)
br=broad (in relation to NMR)
d=doublet (in relation to NMR)
dd=doublet of doublets (in relation to NMR)
Et=ethyl
eq.=equivalents
GC=gas chromatography
h=hour(s)

HPLC=high performance liquid chromatography
IMS=industrial methylated spirit
IPA=iso-propyl alcohol
m=multiplet (in relation to NMR)
Me=methyl
min.=minute(s)
m.p.=melting point
MS=mass spectroscopy
Pd/C=palladium on carbon
q=quartet (in relation to NMR)
rt=room temperature
s=singlet (in relation to NMR)
t=triplet (in relation to NMR)

Prefixes n-, s-, i-, t- and tert- have their usual meanings: normal, secondary, iso, and tertiary.

Example 1 a) [2-(9-Oxa-3,7-diazabicyclo[3.3.1]non-3-yl)-ethyl]-carbamic acid tert-butyl ester 2,4,6-trimethylbenzenesulfonic acid salt

[2-(7-Benzyl-9-oxa-3,7-diazabicyclo[3.3.1]non-3-yl)-ethyl]-carbamic acid tert-butyl ester 2,4,6-trimethylbenzenesulfonic acid salt (150 g prepared as described below), 4-methyl-2-pentanol (MIBC) (300 mL) and methanol (300 mL) were combined in a metal hydrogenation vessel. Solid 5% Pd/C catalyst (4.5 g, 61% water wet, Johnson Matthey type 440L) was added. The mixture was then hydrogenated under 2.5 bar of hydrogen pressure and was simultaneously heated to 55° C. Gas uptake measurement showed the reaction to be complete after 2 hours. After cooling to 40° C. the catalyst was removed by filtration through a glass fibre filter paper. The catalyst was washed on the filter with MIBC (300 mL) and the washings added to the main filtrate. Solvent (185 mL) was removed by distillation at atmospheric pressure. More solvent (243 mL) was then removed by reduced pressure (<100 mmHg) distillation. Isopropyl ether (IPE) (1050 mL) was added quickly at 70° C., which caused the temperature to fall to 45° C. An unstirrable precipitate formed in the reaction vessel. The mixture was re-heated and solvent distilled and collected (268 mL). MIBC (150 mL) was added and at 80° C. all material dissolved. The ratio of MIBC:IPE was now approximately 4:5. The solution was allowed to cool and was seeded (86 mg) at 70° C. The reaction was left to cool overnight to ambient temperature. The mixture was cooled to 8° C. and then the solid product collected by filtration. The solid was washed on the filter with IPE (450 mL) and then sucked dry. Further drying in vacuo at 60° C. gave the title compound as a white solid (115.0 g, 91%).

m.p. 147-9° C.

b) Tert-Butyl 2-{7-[(2S)-3-(4-cyanophenoxy)-2-hydroxypropyl]-9-oxa-3,7-diazabicyclo[3.3.1]non-3-yl}ethylcarbamate Aqueous sodium carbonate solution (1M, 53 mL) was added to a solution of [2-(9-oxa-3,7-diazabicyclo[3.3.1]non-3-yl)-ethyl]-carbamic acid tert-butyl ester 2,4,6-trimethyl-benzenesulfonic acid salt (50.0 g) in water (100 mL). Solid 4-[(2S)-oxiranylmethoxy]benzonitrile (19.1 g) was added and was rinsed into the reaction flask with water (50 mL). The reaction was heated to 75° C. for 3 hours and then left to stir at ambient temperature overnight. Toluene (350 mL) was added followed by aqueous sodium hydroxide (2M, 90 mL). The mixture was stirred for 5 minutes and then the phases were separated. The aqueous phase was discarded and the toluene phase washed with aqueous citric acid (10% w/v, 180 mL). The toluene phase was discarded. MIBC (240 mL) and aqueous sodium hydroxide (5M, 180 mL) were added to the citric acid phase. After mixing well the phases were separated and the aqueous discarded. The MIBC was washed with aqueous sodium chloride (20% w/v, 50 mL). The MIBC was concentrated under vacuum at <55° C. Solvent was collected (water 13 mL, MIBC 29 mL). The MIBC solution was cooled to ambient temperature and filtered, washing through with MIBC (50 mL). Solvent (152 mL) was distilled under vacuum at <66° C. and then distillation was stopped. IPE (360 mL) was added causing the temperature to fall from 65° C. to 37° C. After stirring for 15 minutes T fell by 2° C. to 35° C. and crystallisation started. The mixture was left to cool to ambient temperature overnight with stirring. The mixture was cooled to 5° C. and the product collected by filtration. The solid was washed on the filter with IPE (150 mL) and sucked dry. Further drying in vacuo at 55° C. gave the title compound as a white solid (41.2 g, 87%).

Preparation of [2-(7-Benzyl-9-oxa-3,7-diazabicyclo[3.3.1]non-3-yl)ethyl]-carbamic acid tert-butyl ester, 2,4,6-trimethylbenzenesulfonic acid salt a) 2-(tert-Butyloxycarbonylamino)ethyl 2,4,6-trimethylbenzenesulfonate Triethylamine (65 mL, 465.3 mmole, 1.5 eq) was added in one portion to a solution of tert-butyl N-(2-hydroxyethyl)carbamate (50.11 g, 310.2 mmole, 1.0 eq.) in dichloromethane (250 mL, 5 vols). The solution was cooled to −10° C. and trimethylamine hydrochloride (14.84 g, 155.1 mmole, 0.5 eq.) was added in one portion. The resultant mixture was cooled further to −15° C., stirred for 5 minutes, then treated with a solution of mesitylenesulfonyl chloride (74.74 g, 341.2 mmole, 1.1 eq) in dichloromethane (250 mL, 5 vols), over 28 minutes such that the internal temperature remained below −10° C. Once the addition was complete a precipitate had formed and the mixture was stirred at −10° C. for a further 30 minutes. Water (400 mL, 8 vols) was added and all of the precipitate dissolved. The mixture was stirred rapidly for 5 minutes, and then the two layers were separated. A solvent swap from dichloromethane to IPA was carried out by distillation at reduced pressure. Solvent was removed (450 mL) and replaced with IPA (450 mL) (initial pressure was 450 mbar, b.p. 24° C.; final pressure was 110 mbar, b.p. 36° C.). At the end of the distillation, solvent (150 mL) was removed to bring the volume down to 350 mL (7 vols with respect to the amount of tert-butyl N-(2-hydroxyethyl)carbamate used). The solution was cooled to 25° C., then water (175 mL) was added slowly with stirring, causing the solution gradually to turn cloudy. No solid had precipitated at this stage. More water (125 mL) was added, and a solid precipitate started to form after about 75 mL had been added. The internal temperature rose from 25° C. to 31° C. The mixture was stirred slowly and cooled to 7° C. The solid was collected by filtration, washed with IPA:water (1:1, 150 mL) and dried in vacuo at 40° C. for 21 hours to give the title compound as a white crystalline solid (92.54 g, 87%).

m.p. 73.5° C.

$^1$-NMR (300 MHz, CDCl$_3$) δ 1.42 (9H, s), 2.31 (3H, s), 2.62 (6H, s) 3.40 (2H, q), 4.01 (2H, t), 4.83 (1H, bs), 6.98 (2H, s)

b) 3-Benzyl-9-oxa-3,7-diazabicyclo[3.3.1]nonane b (i) N,N-Bis(2-oxiranylmethyl)benzenesulfonamide Water (2.5 L, 10 vol.) followed by epichlorohydrin (500 mL, 4 eq.) were added to benzenesulfonamide (250 g, 1 eq.). The reactants were heated to 40° C. Aqueous sodium hydroxide (130 g in 275 mL of water) was added such that the temperature of the reaction remained between 40° C. and 43° C. This took approximately 2 hours. (The rate of sodium hydroxide addition needs to be slower at the start of the addition than at the end in order to keep within the temperature range stated.) After the addition of sodium hydroxide was complete, the reaction was stirred at 40° C. for 2 hours, then at ambient temperature overnight. The excess epichlorohydrin was removed as a water azeotrope by vacuum distillation (ca. 4 kPa (40 mbar), internal temp 30° C.), until no more epichlorohydrin distilled. Dichloromethane (1 L) was added and the mixture stirred rapidly for 15 minutes. The phases were allowed to separate (this took 10 minutes although totally clear phases are obtained after standing overnight). The phases were separated and the dichloromethane solution used in the subsequent step below.

$^1$H NMR (400 MHz, CDCl$_3$): δ 2.55-2.65 (2H, m), 2.79 (2H, t, J4A), 3.10-3.22 (4H, m), 3.58-3.73 (2H, m), 7.50-7.56 (2H, m), 7.58-7.63 (1H, m), 7.83-7.87 (2H, m).

b (ii) 5-Benzyl-3,7-dihydroxy-1-phenylsulfonyl-1,5-diazacyclooctane

IMS (2.5 L, 10 vol) was added to the dichloromethane solution from step (i) above. The solution was distilled until the internal temperature reached 70° C. Approximately 1250 mL of solvent was collected. More IMS (2.5 L, 10 vol) was added followed by benzylamine (120 mL, 0.7 eq.) in one portion (no exotherm seen), and the reaction was heated at reflux for 6 hours (no change from 2 hour sampling point). More benzylamine was added (15 mL) and the solution was heated for a further 2 hours. The IMS was distilled off (ca. 3.25 L) and toluene was added (2.5 L). More solvent was distilled (ca. 2.4 L) and then further toluene added (1 L). The head temperature was now 110° C. A further 250 mL of solvent was collected at 110° C. Theoretically, this left the product in ca. 2.4 L of toluene at 110° C. This solution was used in the next step.

$^1$H NMR (400 MHz, CDCl$_3$): δ 7.83-7.80 (4H, m, ArH), 7.63-7.51 (6H, m, ArH), 7.30-7.21 (10H, ArH), 3.89-3.80 (4H, m, CH(a)+CH(b)), 3.73 (2H, S, CH$_2$Ph(a)), 3.70 (2H, s, CH$_2$Ph(b)), 3.59 (2H, dd, CHHNSO$_2$Ar(a)), 3.54 (2H, dd, CHHNSO$_2$Ar(b)), 3.40 (2H, dd, CHHNSO$_2$Ar(b)), 3.23 (2H, dd, CHHNSO$_2$Ar(a)), 3.09-2.97 (4H, m, CHHNBn(a)+CHHNBn(b)), 2.83 (2H, dd, CHHNBn(b)), 2.71 (2H, dd, CHHNBn(a)) (Data taken from purified material comprising a 1:1 mixture of trans- (a), and cis-diol (b))

b (iii) 3-Benzyl-7-(phenylsulfonyl)-9-oxa-3,7-diazabicyclo[3.3.1]nonane

The toluene solution from the previous step (ii) above was cooled to 50° C. Anhydrous methanesulfonic acid (0.2 L) was added. This caused a temperature rise from 50° C. to 64° C. After 10 minutes, methanesulfonic acid was added (1 L) and the reaction heated to 110° C. for 5 hours. Toluene was then distilled from the reaction; 1.23 L was collected. (Note that the internal temperature should not be allowed higher than 110° C. at any stage otherwise the yield will be decreased.) The reaction was then cooled to 50° C. and a vacuum applied to remove the rest of the toluene. Heating to 110° C. and 65 kPa (650 mbar) allowed a further 0.53 L to be removed. (If the toluene can be removed at a lower temperature and pressure then that is beneficial.) The reaction was then left to cool to 30° C. and deionised water (250 mL) was added. This caused the temperature to rise from 30° C. to 45° C. More water (2.15 L) was added over a total time of 30 minutes such that the temperature was less than 54° C. The solution was cooled to 30° C. and then dichloromethane (2 L) was added. With external cooling and rapid stirring, the reaction mixture was basified by adding aqueous sodium hydroxide (10 M, 2 L) at a rate that kept the internal temperature below 38° C. This took 80 minutes. The stirring was stopped and the phases separated in 3 minutes. The layers were partitioned. IMS (2 L) was added to the dichloromethane solution and distillation started. Solvent (2.44 L) was collected until the head temperature reached 70° C. Theoretically, this left the product in 1.56 L of IMS. The solution was then allowed to cool to ambient temperature overnight with slow stirring. The solid product that precipitated was filtered and washed with IMS (0.5 L) to give a fawn-coloured product that, on drying at 50° C., in vacuum, gave 50.8 g (8.9% over 3 steps).

20.0 g of this product was dissolved in acetonitrile (100 mL) at reflux to give a pale yellow solution. After cooling to ambient temperature, the crystals that formed were collected by filtration and washed with acetonitrile (100 mL). The product was dried in vacuo at 40° C for 1 hour to give 17.5 g (87%) of sub-title compound.

$^1$H NMR (400 MHz, CDCl$_3$): δ 7.18-7.23 (10H, m), 3.86-3.84 (2H, m), 3.67 (2H, d), 3.46 (2H, s), 2.91 (2H, d), 2.85 (2H, dd), 2.56 (2H, dd)

b (iv) 3-Benzyl-9-oxa-3,7-diazabicyclo[3.3.1]nonane dihydrochloride

Concentrated hydrobromic acid (1.2 L, 3 rel. vol.) was added to solid 3-benzyl-7-(phenylsulfonyl)-9-oxa-3,7-diazabicyclo[3.3.1]nonane (400 g, see step (iii) above) and the mixture was heated to reflux under a nitrogen atmosphere. The solid dissolved in the acid at 95° C. After heating the reaction for 8 hours, HPLC analysis showed that the reaction was complete. The contents were cooled to room temperature. Toluene (1.2 L, 3 rel. vol.) was added and the mixture stirred vigorously for 15 minutes. Stirring was stopped and the phases were partitioned. The toluene phase was discarded along with a small amount of interfacial material. The acidic phase was returned to the original reaction vessel and sodium hydroxide (10 M, 1.4 L, 3.5 rel. vol.) was added in one portion. The internal temperature rose from 30° C. to 80° C. The pH was checked to ensure it was >14. Toluene (1.6 L, 4 rel. vol.) was added and the temperature fell from 80° C. to 60° C. After vigorous stirring for 30 minutes, the phases were partitioned. The aqueous layer was discarded along with a small amount of interfacial material. The toluene phase was returned to the original reaction vessel, and 2-propanol (4 L, 10 rel. vol.) was added. The temperature was adjusted to between 40° C. and 45° C. Concentrated hydrochloric acid (200 mL) was added over 45 minutes such that the temperature remained at between 40° C. and 45° C. A white precipitate formed. The mixture was stirred for 30 minutes and then cooled to 7° C. The product was collected by filtration, washed with 2-propanol (0.8 L, 2 rel vol.), dried by suction and then further dried in a vacuum oven at 40° C. Yield=297 g (91%).

$^1$H NMR (CD$_3$OD+4 drops D$_2$O): δ 2.70 (br d, 2H), 3.09 (d, 2H), 3.47 (br s, 4H), 3.60 (s, 2H), 4.12 (br s, 2H), 7.30-7.45 (m, 5H).
API MS: m/z=219 [C$_{13}$H$_{18}$N$_2$O+H]$^+$.

B (v) 3-Benzyl-9-oxa-3,7-diazabicyclo[3.3.1]nonane

All volumes and equivalents are measured with respect to the amount of 3-benzyl-9-oxa-3,7-diazabicyclo[3.3.1] nonane dihydrochloride (see step (iv) above) used. Toluene (420 mL, 7 vols) and aqueous sodium hydroxide solution (2M, 420 mL, 7 vols, 4.0 eq) were added to 3-benzyl-9-oxa-3,7-diazabicyclo[3.3.1]nonane dihydrochloride (60.07 g, 206.03 mmole, 1.0 eq., see step (iv) above). The mixture was stirred under nitrogen, heated to 60° C. and held at this temperature for 30 minutes by which time two clear layers had formed. The lower, aqueous layer was removed, and the toluene solution of title compound (free base) was azeodried at atmospheric pressure (total volume of solvent removed=430 mL; total volume of toluene added=430 mL), then concentrated to a volume of 240 mL (4 vols). Karl Fischer analysis at this stage showed 0.06% water in the solution. The dried solution of title compound (theoretically 44.98 g, 206.03 mmole, 1.0 eq) was used as such in a subsequent step.

c) [2-(7-Benzyl-9-oxa-3,7-diazabicyclo[3.3.1]non-3-yl)ethyl]carbamic acid tert-butyl ester, 2,4,6-trimethylbenzenesulfonic acid salt A warm (28° C.) solution of 2-(tert-butyloxycarbonylamino)ethyl 2,4,6-trimethylbenzenesulfonate (70.93 g, 206.03 mmole, 1.0 eq, see Preparation a above) in toluene (240 mL 4 vols), was added to a solution of 3-benzyl-9-oxa -3,7-diazabicyclo[3.3.1]nonane (44.98 g, 206.03 mmole, 1.0 eq. in toluene (240 mL, 4 vols) (see Preparation b (v) above). The resultant solution was stirred rapidly under nitrogen, with heating at 68° C. for 8 hours. The reaction was left to stir at ambient temperature for 84 hours. A thick, white solid precipitate had formed in a pale yellow solution. The mixture was cooled to +9° C., and title compound was collected by filtration. The reaction vessel was washed with toluene (100 mL) and added to the filter. The filter cake was washed with toluene (150 mL). The white solid product was suction dried for 15 minutes, then dried to constant weight in vacuo at 40° C. for 23 hours. The yield of title compound obtained was 79.61 g, 141.7 mmole, 69%. The combined filtrate and washings (670 mL) were washed with aqueous sodium hydroxide solution (2M, 200 mL, 3.3 vols). The mixture was heated to 60° C., and held at this temperature for 20 minutes with rapid stirring. The two layers were then separated. The toluene solution was concentrated to 200 mL by vacuum distillation (bp 50-54° C. at 650-700 mbar; bp 46° C. at 120 mbar at the end). As the distillation progressed, the solution became cloudy due to the formation of title compound. It was assumed that 20% of the original amount of 3-benzyl-9-oxa-3,7-diazabicyclo [3.3.1]nonane remained in the filtrate, and so extra 2-(tert-butyloxycarbonylamino)ethyl 2,4,6-trimethylbenzenesulfonate (14.20 g, 41.21 mmole, 0.2 eq) was added in one portion (charged as a solid rather than as a solution in toluene). The cloudy solution was heated at 67° C. for 8 hours with rapid stirring, and then left to stir at ambient temperature for 11 hours. The mixture was cooled to +8° C., and title compound was collected by filtration. The reaction vessel was washed with more toluene (2×30 mL), and added to the filter. The white solid product was suction dried for 15 minutes, then dried to constant weight in vacuo at 40° C. for 7 hours. The yield of title compound was 23.25 g, 41.39 mmole, 20%. The combined yield of title compound (a white solid) was 102.86 g, 183.11 mmole, 89%.

m.p. 190-190.5° C. $^1$H-NMR (300MHz, CDCl$_3$) δ 1.43 (9H, s), 2.17 (3H, s), 2.51 (6H, s), 2.73-2.80 (2H, m), 2.90-2.94 (4H, m), 3.14-3.22 (4H, m), 3.37 (2H, bm), 3.89 (2H, bs), 4.13 (2H, bs), 6.74 (2H, s), 7.12 (1H, bt), 7.42-7.46 (5H, m)

The invention claimed is:
1. An acid addition salt of a compound of Formula I

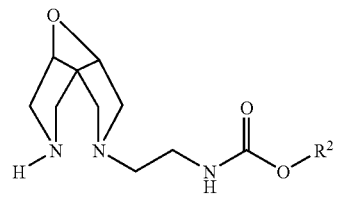

I wherein R$^2$ represents C$_{1-6}$ alkyl (optionally substituted by one or more substituents selected from —OH, halo, cyano, nitro and aryl) or aryl, wherein each aryl and aryloxy group, is optionally substituted.

2. A salt according to claim 1, wherein the acid component of the acid addition salt is represented by formula A

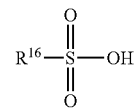

A wherein R$^{16}$ represents unsubstituted C$_{1-4}$ alkyl, C$_{1-4}$ perfluoroalkyl or phenyl, which latter group is optionally substituted by one or more substituents selected from C$_{1-6}$ alkyl, halo, nitro and C$_{1-6}$ alkoxy.

3. A salt according to claim 2, wherein the salt is a toluenesulfonate, benzenesulfonate, nosylate, brosylate, besylate or mesitylate salt.

4. A salt according to claim 1, wherein the salt is in solid form.

5. A salt according to claim 1, wherein the salt is [2-(9-oxa-3,7-diazabicyclo[3.3.1]non-3-yl)-ethyl]-carbamic acid tert-butyl ester 2,4,6-trimethylbenzenesulfonic acid.

6. A process for the preparation of a compound of Formula II

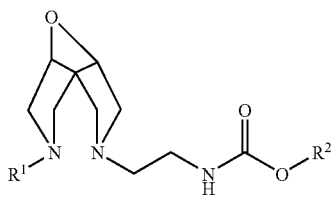

II wherein $R^1$ represents a moiety of formula Ia

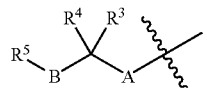

wherein A represents $CH_2$ and $R^3$ represents —OH or —N(H)$R^7$;

$R^4$ represents H, $C_{1-6}$ alkyl or, together with $R^3$, represents =O;

$R^5$ represents phenyl or pyridyl, optionally substituted by one or more substituents selected from —OH, cyano, halo, nitro, $C_{1-6}$ alkyl (optionally terminated by —N(H)C(O)O$R^{13a}$), $C_{1-6}$ alkoxy, —N($R^{14a}$)$R^{14b}$, —C(O)$R^{14c}$, —C(O)O$R^{14d}$, —C(O)N($R^{14e}$)$R^{14f}$, —N($R^{14g}$)C(O)$R^{14h}$, —N($R^{14i}$)C(O)N($R^{14j}$)$R^{14k}$, —N($R^{14m}$)S(O)$_2R^{13b}$, —S(O)$_2R^{13c}$ and —OS(O)$_2R^{13d}$;

$R^7$ represents H, $C_{1-6}$ alkyl, —E-aryl, —E-Het$^1$, —C(O)$R^{9a}$, —C(O)O$R^{9b}$, —S(O)$_2R^{9c}$, —[C(O)]$_p$N($R^{10a}$)$R^{10b}$ or —C(NH)NH$_2$;

$R^{9a}$ to $R^{9d}$ represent, independently at each occurrence, $C_{1-6}$ alkyl (optionally substituted by one or more substituents selected from halo, aryl and Het$^2$), aryl, Het$^3$, or $R^{9a}$ and $R^{9d}$ independently represent H;

$R^{10a}$ and $R^{10b}$ independently represent, at each occurrence, H or $C_{1-6}$ alkyl (optionally substituted by one or more substituents selected from halo, aryl and Het$^4$), aryl, Het$^5$, or together represent $C_{3-6}$ alkylene, optionally interrupted by an O atom;

E represents, independently at each occurrence, a direct bond or $C_{1-4}$ alkylene;

B represents —Z—, —Z-N($R^{12}$)—, —N($R^{12}$)-Z—, —Z-S(O)$_n$— or —Z-O— (in which latter two groups, Z is attached to the carbon atom bearing $R^3$ and $R^4$);

Z represents a direct bond or $C_{1-4}$ alkylene;

$R^{11}$ and $R^{12}$ independently represent H or $C_{1-6}$ alkyl;

$R^{13a}$ to $R^{13d}$ independently represent $C_{1-6}$ alkyl;

$R^{14a}$ and $R^{14b}$ independently represent H, $C_{1-6}$ alkyl or together represent $C_{3-6}$ alkylene, resulting in a four- to seven-membered nitrogen-containing ring;

$R^{14c}$ to $R^{14m}$ independently represent H or $C_{1-6}$ alkyl;

n represents 0, 1 or 2;

p represents 1 or 2;

Het$^1$ to Het$^5$ represent, independently at each occurrence, five- to twelve-membered heterocyclic groups containing one or more heteroatoms selected from oxygen, nitrogen and sulfur, which heterocyclic groups are optionally substituted by one or more substituents selected from =O, —OH, cyano, halo, nitro, $C_{1-6}$ alkyl, $C_{1-6}$ alkoxy, aryl, aryloxy, —N($R^{15a}$)$R^{15b}$, —C(O)$R^{15c}$, —C(O)O$R^{15d}$, —C(O)N($R^{15e}$)$R^{15f}$, —N($R^{15g}$)C(O)$R^{15h}$ and —N($R^{15i}$)S(O)$_2R^{15j}$;

$R^{15a}$ to $R^{15j}$ independently represent $C_{1-6}$ alkyl, aryl or $R^{15a}$ to $R^{15i}$ independently represent H; and $R^2$ represents $C_{1-6}$ alkyl (optionally substituted by one or more substituents selected from —OH, halo, cyano, nitro and aryl) or aryl, wherein each aryl and aryloxy group is optionally substituted.

wherein a salt of a compound of Formula I

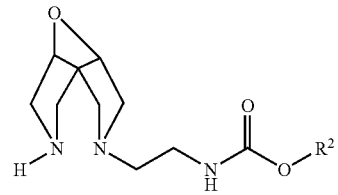

wherein $R^2$ is as previously defined is reacted with a compound of Formula III

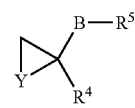

wherein Y represents O or N($R^7$) and $R^4$, $R^5$, $R^7$ and B are as hereinbefore defined, at a temperature in the range of 0° C. to 100° C. in the presence of a water and in the presence of a base.

7. A process according to claim 6, wherein the salt has been previously isolated in solid form.

8. A process according to claim 6 for the preparation of tert-butyl 2-{7-[(2S)-3-(4-cyanophenoxy)-2-hydroxypropyl]-9-oxa-3,7-diaza-bicyclo[3.3.1]-non-3-yl}ethylcarbamate which comprises reacting a salt of [2-(9-oxa-3,7-diazabicyclo[3.3.1]non-3-yl)-ethyl]-carbamic acid tert-butyl ester with 4-[(2S)-oxiranylmethoxy]benzonitrile at a temperature in the range of 0° C. to 100° C. in the presence of water and in the presence of a base.

9. A process according to claim 6, wherein the salt of Formula I is an isolated salt of [2-(9-oxa-3,7-diazabicyclo[3.3.1]non-3-yl)-ethyl]-carbamic acid tert-butyl ester.

10. A process according to claim 9, wherein the salt is the 2,4,6-trimethylbenzenesulfonic acid salt.

* * * * *